(12) United States Patent
Pomerantz et al.

(10) Patent No.: US 7,142,358 B2
(45) Date of Patent: Nov. 28, 2006

(54) GEM MICROSCOPE WITH PORTABILITY KIT

(75) Inventors: Howard Pomerantz, Newport Beach, CA (US); Sherman Gingerella, Carlsbad, CA (US); Derwin Fritts, Carlsbad, CA (US)

(73) Assignee: Gemological Institute of America, Inc., Carlsbad, CA (US)

( * ) Notice: Subject to any disclaimer, the term of this patent is extended or adjusted under 35 U.S.C. 154(b) by 0 days.

(21) Appl. No.: 10/935,405

(22) Filed: Sep. 7, 2004

(65) Prior Publication Data

US 2005/0083569 A1  Apr. 21, 2005

Related U.S. Application Data

(60) Provisional application No. 60/501,604, filed on Sep. 9, 2003.

(51) Int. Cl.
*G02B 21/00* (2006.01)
*G02B 21/26* (2006.01)
(52) U.S. Cl. ............... 359/368; 359/382; 359/391
(58) Field of Classification Search ........ 359/368–390, 359/391–394, 800–819
See application file for complete search history.

(56) References Cited

U.S. PATENT DOCUMENTS

| 2,533,747 | A | * | 12/1950 | Thienemann | ............... 359/804 |
| 4,262,426 | A | * | 4/1981 | Miyazaki | .................... 359/368 |
| 5,270,855 | A | * | 12/1993 | Hasegawa | ................... 359/368 |
| 5,844,714 | A | * | 12/1998 | DiResta | ...................... 359/368 |
| 5,971,536 | A | * | 10/1999 | Chiu | .......................... 351/41 |
| 6,322,223 | B1 | | 11/2001 | Smith et al. | ................ 359/871 |
| 6,693,741 | B1 | * | 2/2004 | Sukekawa | ................... 359/368 |

* cited by examiner

*Primary Examiner*—Thong Q Nguyen
(74) *Attorney, Agent, or Firm*—DLA Piper Rudnick Gray Cary US LLP

(57) ABSTRACT

A gem microscope according to the invention includes a focus column, a stage, and a quick disconnect mechanism that facilitates removable coupling of the focus column to the stage. The focus column and the stage have compatible features that establish the proper mounting plane and lateral alignment of the focus column relative to the stage. In the example embodiment, the quick disconnect mechanism includes a threaded element on the focus column and a compatibly threaded thumbwheel that rotates within the stage to connect/disconnect the focus column to/from the stage.

23 Claims, 5 Drawing Sheets

GEM MICROSCOPE WITH PORTABILITY KIT

CROSS REFERENCE TO RELATED APPLICATIONS

This application claims the benefit of U.S. provisional patent application Ser. No. 60/501,604, filed Sep. 9, 2003, titled GEM MICROSCOPE.

FIELD OF THE INVENTION

The present invention relates generally to microscopes. More particularly, the present invention relates to a gem microscope, suitable for use in a laboratory environment, that can be quickly disassembled for storage or transportation.

BACKGROUND OF THE INVENTION

The prior art is replete with different types of microscopes. Gem microscopes are precision instruments that provide specific lighting and viewing conditions for magnified viewing of gems and jewels. Gem microscopes are widely used by gemological researchers, diamond graders, and jewelers. Such microscopes are commercially available from GIA GEM INSTRUMENTS and other manufacturers.

Precision, laboratory grade gem microscopes are normally intended for stationary use in a somewhat permanent location, e.g., on a lab workstation. Such gem microscopes, which can be physically large in size and somewhat heavy and bulky, are not intended to be used as portable instruments that can be easily transported from one site to another. On the other hand, portable versions of gem microscopes may not have the precise optical alignment and sturdiness found in the "desktop" versions.

Accordingly, it would be desirable to have a precision gem microscope that can be quickly and easily disassembled for storage and transportation, and quickly and easily reassembled in a way that maintains the desired optical alignment. Thus, it is desired that the focus column be orthogonal to the stage and the optical unit be centered above the center of the dark field despite the quick assembly and disassembly.

BRIEF SUMMARY OF THE INVENTION

A gem microscope configured in accordance with the invention generally includes a focus column for an optical head, a stage, and a base connected to the stage. The focus column can be removed from the stage for storage and transportation of the gem microscope. The gem microscope employs a quick disconnect structure that can be manipulated to connect/disconnect the focus column to/from the stage. In one example embodiment, the quick disconnect structure includes a threaded element extending from the focus column and a threaded thumbwheel that engages the threaded element to hold the focus column against the stage.

The above and other aspects of the present invention may be carried out in one form by a gem microscope subassembly comprising a focus column having a lower end, a stage having a pocket formed therein for receiving the lower end of the focus column, and a quick disconnect mechanism for removable coupling of the focus column to the stage. The quick disconnect mechanism is externally accessible to a user. This external access facilitates quick and easy disassembly and reassembly of a gem microscope that incorporates the subassembly.

BRIEF DESCRIPTION OF THE DRAWINGS

A more complete understanding of the present invention may be derived by referring to the detailed description and claims when considered in conjunction with the following Figures, wherein like reference numbers refer to similar elements throughout the Figures.

DETAILED DESCRIPTION OF A PREFERRED EMBODIMENT

It should be appreciated that the particular implementations shown and described herein are illustrative of the invention and its best mode and are not intended to otherwise limit the scope of the invention in any way. Indeed, for the sake of brevity, conventional aspects of gem microscopes (and the individual operating components of gem microscopes) may not be described in detail herein.

Figure 1:
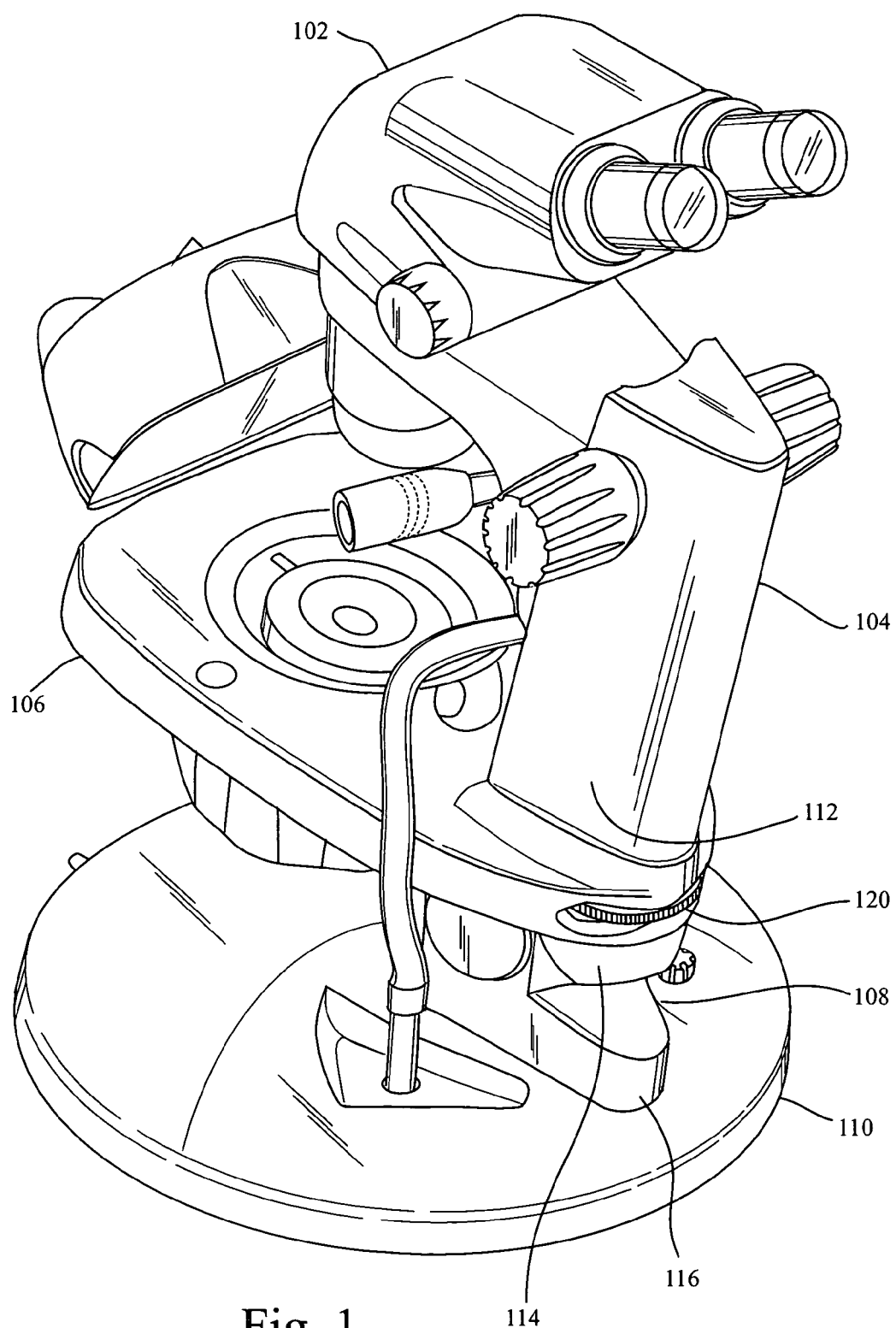
FIG. 1 is a perspective view of a gem microscope configured in accordance with the invention.
Figure 2:
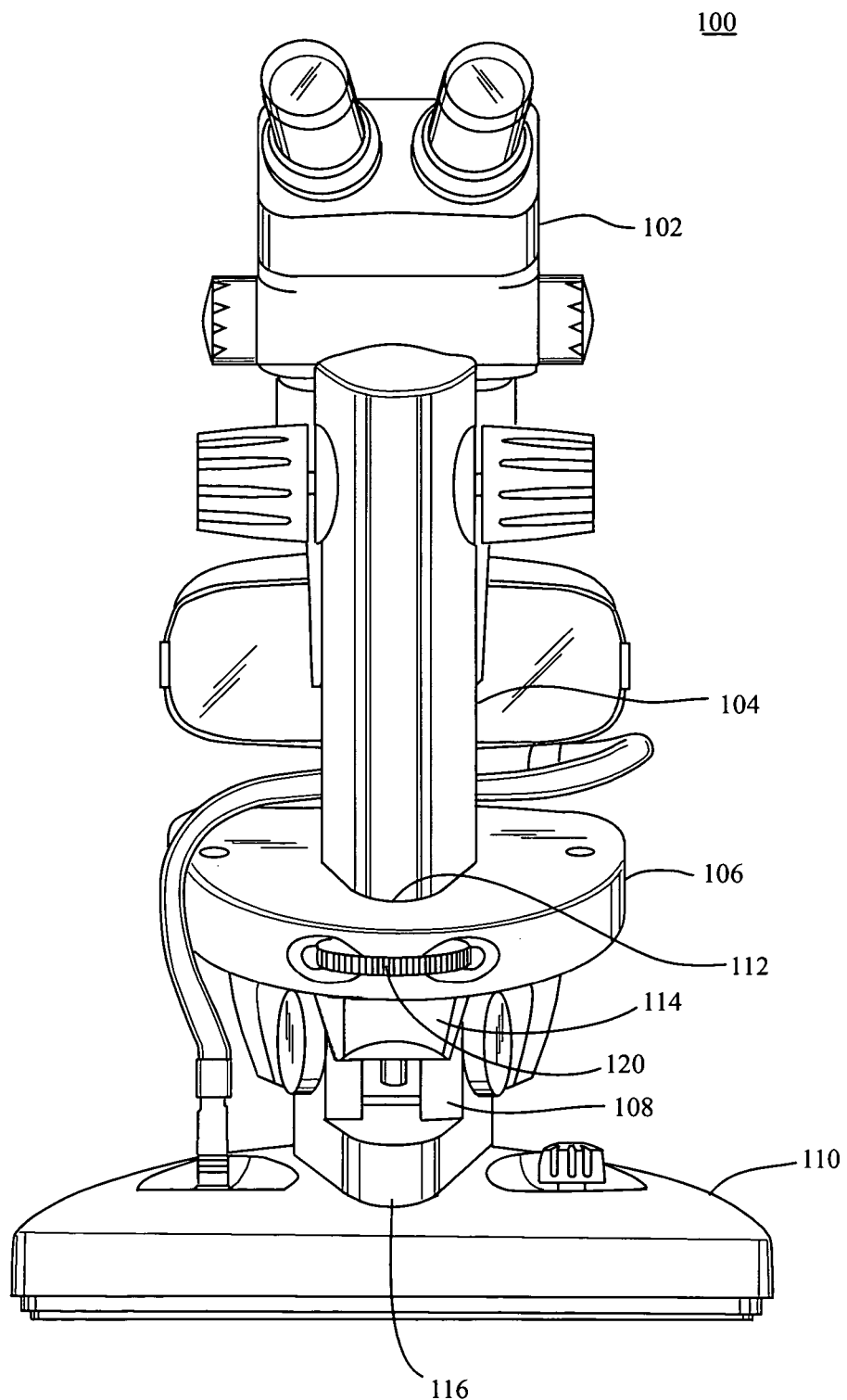
FIG. 2 is a rear elevation view of the gem microscope shown in FIG. 1.

FIG. 1 is a perspective view, and FIG. 2 is a rear elevation view, of a gem microscope 100 configured in accordance with the invention. Gem microscope 100 generally includes an optical assembly 102, a focus column 104, a stage 106, a knuckle joint 108, and a base structure 110. Optical assembly 102 is coupled to focus column 104, and the two components are suitably configured to allow positional adjustment of optical assembly 102 relative to focus column 104 (along the longitudinal axis of focus column 104). In turn, the lower end 112 of focus column 104 is mounted to stage 106. In this manner, stage 106 is coupled to optical assembly 102. In the example embodiment shown in FIG. 2, lower end 112 is mounted to stage 106 near knuckle joint 108.

Knuckle joint 108 includes at least two components: a first component 114 and a second component 116. First component 114 is suitably coupled to stage 106, while second component 116 is suitably coupled to base structure 110. First component 114 and second component 116 are coupled together to form a hinge that facilitates tilt adjustments for gem microscope 100. Base structure 110 generally provides a stable and solid foundation for gem microscope 100, which is desirable when viewing valuable gems, when making precise measurements, or when viewing gems in connection with grading.

Figure 3:
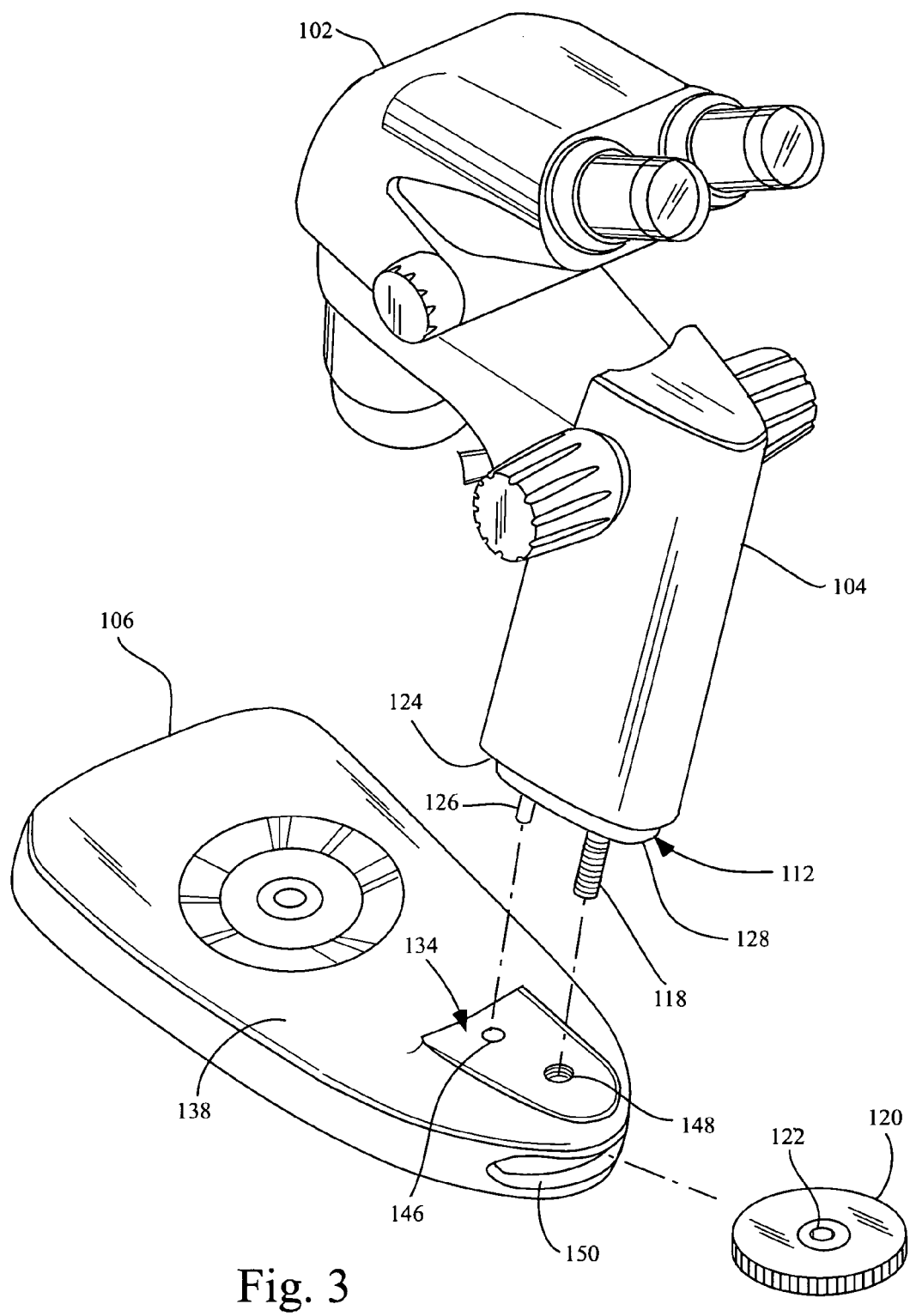
FIG. 3 is an exploded perspective view of a portion of the gem microscope shown in FIG. 1.

As described in more detail below, gem microscope 100 includes a quick disconnect feature that facilitates easy disassembly of gem microscope 100 for storage or transport. In accordance with conventional gem microscopes, optical assembly 102 can be removed from focus column 104, preferably by decoupling a screw. In addition, focus column 104 can be removed from stage 106 as depicted in FIG. 3. After disassembly, gem microscope 100 can be handled as three main assemblies: optical assembly 102, focus column 104, and the lower structure, which includes stage 106, knuckle joint 108, and base structure 110.

In accordance with the example embodiment shown in the figures, focus column 104 is secured to stage 106 with a quick disconnect mechanism that includes a threaded element 118 mounted to (and protruding from) the lower end 112 of focus column, and a thumbwheel 120 having a threaded insert 122 compatible with threaded element 118. In alternate embodiments, the quick disconnect mechanism may include one or more latches, clips, levers, screws, or the like. The quick disconnect mechanism may also include structures on the focus column and/or stage that facilitate a press-fit, snap-fit, or slide-fit assembly of those two components.

Figure 4:
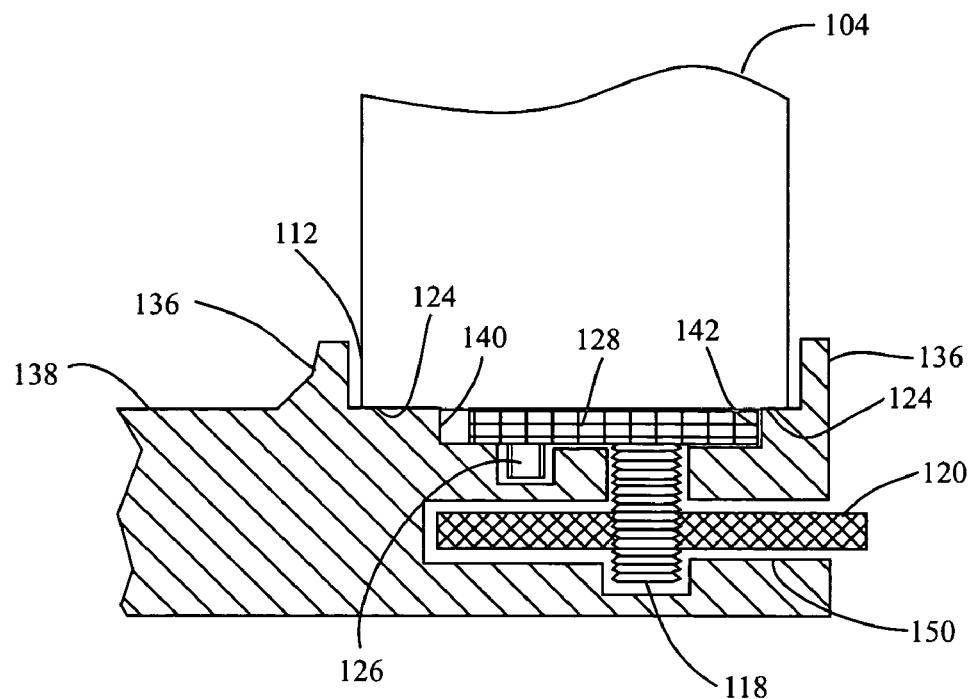
FIG. 4 is a side cross sectional view of a portion of the gem microscope shown in FIG. 1.
Figure 5:
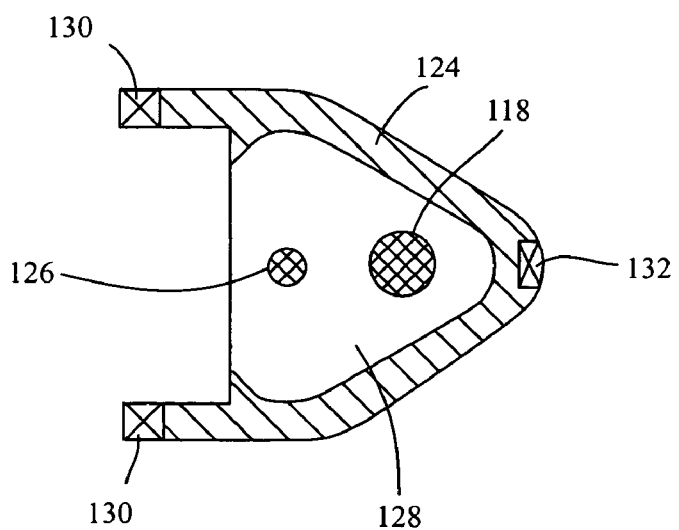
FIG. 5 is an end view of a focus column suitable for use with the gem microscope shown in FIG. 1.
Figure 6:
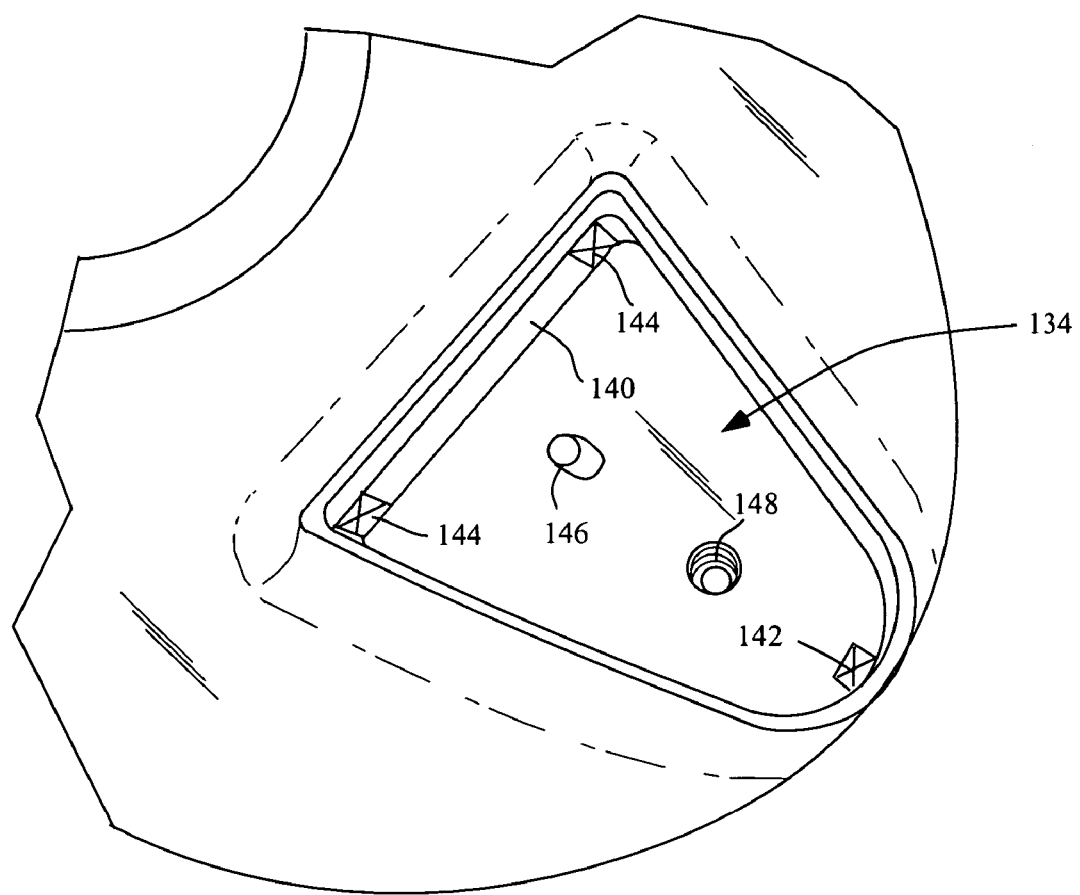
FIG. 6 is a top perspective view of a stage suitable for use with the gem microscope shown in FIG. 1.

Referring to FIGS. 3–6, certain details of focus column 104 and stage 106 will be described in connection with the example quick disconnect mechanism. FIG. 3 is a cross sectional view of the junction of focus column 104 and stage 106, as viewed from a sectional line that bisects gem microscope 100 from the front to the rear. Focus column 104 includes a mounting surface 124 located at its lower end 112. In this embodiment, mounting surface 124 is smooth and flat, and it defines a plane. As shown in FIG. 5, mounting surface 124 is located around the perimeter of lower end 112. Focus column 104 also includes an alignment pin 126 and threaded element 118 coupled to the lower end 112. In the illustrated embodiment, alignment pin 126 and threaded element 118 are both attached to an adapter plate 128 that is in turn attached to the lower end 112 of focus column 104. Adapter plate 128 may be coupled to focus column 104 with a number of bolts or screws in a pattern that matches a hole pattern in the lower end 112, where the hole pattern corresponds to a conventional pattern that would otherwise be utilized to permanently attach focus column 104 to a stage. In this regard, the focus column itself, without adapter plate 128, need not be modified from existing focus columns found in "permanent" gem microscopes. A standard focus column may be used in an embodiment of the invention. On the bottom of the focus column 104, there are holes 146/148 for coupling the focus column 104 to the stage 106. These holes 146/148 are preferably used to attach the adaptor plate 128 and permit portability.

In the example embodiment, adapter plate 128 is attached against mounting surface 124 such that adapter plate 128 extends beyond the plane of mounting surface 124 (see FIG. 4). Adapter plate 128 has a smaller footprint relative to the footprint of mounting surface 124, as shown in FIG. 5. As described below, certain areas of mounting surface 124 that remain uncovered by adapter plate 128 contact features of stage 106 when gem microscope 100 is assembled. For example, FIG. 5 schematically depicts two forward contact points 130 and one rear contact point 132 on mounting surface 124—these contact points represent sections of mounting surface 124 that make physical contact with corresponding mounting elements on stage 106.

Stage 106 may include a pocket 134 formed therein (or attached thereto). Pocket 134 is suitably shaped and sized to receive the lower end 112 of focus column 104. As shown in FIG. 4, pocket 134 may be defined at least in part by a perimeter wall 136 that stands above the main surface 138 of stage 106. In the preferred embodiment, perimeter wall 136 closely follows the outer contour of lower end 112, and hides the junction of focus column 104 and stage 106, thus serving to provide aesthetic functionality.

Stage 106 includes a number of mounting elements located within pocket 134. The example embodiment employs a forward mounting element 140 and a rear mounting element 142. Forward mounting element 140 forms a ledge against the forward portion of perimeter wall 136, and rear mounting element 142 forms a ledge against the rear portion of perimeter wall 136. When assembled, rear mounting element 142 mates with rear contact point 132, and two contact points 144 on forward mounting element 140 mate with forward contact points 130. These three points of contact establish a mounting plane for focus column 104. This mounting plane is ensure that optical assembly 102 has the proper line of sight alignment relative to the gem viewing position, i.e., that the plane of the stage is orthogonal to the focus column 104. Threaded protruding element 118 serves to secure and position the focus column 104 with the stage 106, while unthreaded protrusion 126 serves to position the focus column 104 relative to the stage 106. As shown in FIG. 4, when focus column 104 is secured to stage 106, adapter plate 128 is positioned below the mounting plane. In this regard, forward mounting element 140 and rear mounting element 142 serve as stand-off features within pocket 134.

Stage 106 includes a hole or cavity 146 that is sized and shaped to accommodate alignment pin 126. In the example embodiment, hole 146 is located within pocket 134. Hole 146 receives alignment pin 126 to establish lateral alignment of focus column 104 relative to stage 106. Such lateral alignment is important to ensure that optical assembly 102 is properly aligned with the gem viewing position. Hole 146 is one suitable means for receiving alignment pin 126. Alternatively, alignment pin 126 may be received within a suitably configured slot, depression, or cavity formed within the surface of stage 106, or a protrusion or wall formed above the surface of stage 106. Stage 106 also includes a hole 148 that is sized and shaped to receive threaded element 118. In the example embodiment, hole 148 is located within pocket 134. Hole 148 also functions to receive threaded element 118 to establish lateral alignment of focus column 104 relative to stage 106.

Stage 106 preferably includes a cavity 150 formed therein proximate the mounting location for focus column 104. As shown in FIG. 4, at least a portion of cavity 150 is located below pocket 134, and cavity 150 is accessible from the rear of stage 106. Cavity 150 resides below holes 146/148 and hole 148 is arranged to provide access to cavity 150 for threaded element 118. In other words, threaded element 118 can pass through hole 148 and into cavity 150. Cavity 150 is also configured to accommodate thumbwheel 120, as shown in FIGS. 1, 2, and 4. Cavity 150 is sized to allow rotation of thumbwheel 120 for engagement/disengagement with threaded element 118.

In the illustrated embodiment, threaded element 118 and thumbwheel 120 form the quick disconnect mechanism, at least a portion of which is externally accessible to a user. Generally, threaded element 118 is a first coupling element and thumbwheel 120 is a second coupling element that is compatible with the first coupling element. The thumbwheel 120 is configured to engage threaded element 118 to secure focus column 104 to stage 106, and to disengage threaded element 118 to release focus column 104 from stage 106. When engaging threaded element 118, thumbwheel 120 is tightened to pull focus column 104 toward stage 106. Thumbwheel 120 is sized to enable sufficient tightening of focus column 104 by hand.

Disassembly of focus column 104 from stage 106 is accomplished by rotating thumbwheel 120 in the appropriate direction to loosen the threaded engagement. Focus column 104 can be lifted out of pocket 134 while thumbwheel 120 is being loosened. Eventually, thumbwheel 120 completely disengages threaded element 118 and focus column 104 can be removed from stage 106. Assembly of focus column 104 to stage 106 is also straightforward. Thumbwheel 120 is positioned within cavity 150 such that the threaded insert 122 of thumbwheel 120 is aligned with hole 148. Thereafter, focus column 104 is manipulated to insert threaded element 118 into hole 148. Focus column 104 is held in place while rotating thumbwheel 120, thereby tightening the subassembly. During assembly, alignment pin 126 is placed within hole 126 to ensure proper lateral alignment within pocket 134. Finally, thumbwheel 120 is tightened to secure focus column 104 to stage 106.

In practice, gem microscope 100 can be sold or distributed as a "permanent" unit with a nut or attachment means securing threaded element 118 within cavity 150. In such an embodiment, access to threaded element 118 may be restricted by a suitably configured plug, cover plate, or the like. When necessary, the microscope can be converted into a portable unit by removing the plug or cover plate and replacing the nut with thumbwheel 120.

The present invention has been described above with reference to a preferred embodiment. However, those skilled in the art having read this disclosure will recognize that changes and modifications may be made to the preferred embodiment without departing from the scope of the present invention. These and other changes or modifications are intended to be included within the scope of the present invention, as expressed in the following claims.

What is claimed is:

1. A subassembly for a gem microscope, said subassembly comprising:
    a focus column having a lower end, a mounting surface located at said lower end, and a spaced-apart alignment pin and threaded coupling element pair coupled to said lower end;
    a stage for receiving said lower end;
    a number of mounting elements on said stage, said mounting elements being configured to establish a mounting plane for said focus column when in contact with said mounting surface; and
    means, located on said stage, for receiving said spaced-apart alignment pin and threaded coupling element pair to establish lateral alignment of said focus column relative to said stage.

2. A subassembly according to claim 1, wherein said means for receiving said alignment pin comprises a hole formed within said stage.

3. A subassembly according to claim 1, wherein said means for receiving said alignment pin comprises a cavity formed within a surface of said stage.

4. A subassembly according to claim 1, wherein the stage has a pocket formed therein for facilitating the receiving of said lower end.

5. A gem microscope comprising the subassembly recited in claim 1.

6. A subassembly for a gem microscope, said subassembly comprising:
    a focus column having a lower end, a mounting surface located at said lower end, and an alignment pin coupled to said lower end;
    a stage for receiving said lower end;
    a number of mounting elements on said stage, said mounting elements being configured to establish a mounting plane for said focus column when in contact with said mounting surface;
    means, located on said stage, for receiving said alignment pin to establish lateral alignment of said focus column relative to said stage, and
    a quick disconnect mechanism for removably coupling said focus column to said stage, at least a portion of said quick disconnect mechanism being externally accessible to a user.

7. A subassembly according to claim 6, wherein said quick disconnect mechanism comprises a coupling element mounted to, and protruding from, said lower end, said coupling element being configured to further establish lateral alignment of said focus column relative to said stage.

8. A subassembly for a gem microscope, said subassembly comprising:
    a focus column having a lower end, a mounting surface located at said lower end, and an alignment pin coupled to said lower end;
    a stage for receiving said lower end;
    a number of mounting elements on said stage, said mounting elements being configured to establish a mounting plane for said focus column when in contact with said mounting surface; and
    means, located on said stage, for receiving said alignment pin to establish lateral alignment of said focus column relative to said stage, wherein said means for receiving said alignment pin comprises a protrusion formed above a surface of said stage.

9. A subassembly for a gem microscope, said subassembly comprising:
    a focus column having a lower end;
    a stage for receiving said lower end; and
    a threaded quick disconnect mechanism for removably coupling of said focus column to said stage by rotationally mating with a complementary threaded element, said threaded quick disconnect mechanism being externally accessible to a user.

10. A subassembly according to claim 9, further comprising:
    a mounting surface located at said lower end of said focus column; and
    a number of mounting elements on said stage, said mounting elements being configured to establish a mounting plane for said focus column when in contact with said mounting surface.

11. A subassembly according to claim 9, wherein said quick disconnect mechanism comprises:
    a first component coupled to said lower end of said focus column; and
    a second component configured to engage said first component to secure said focus column to said stage and to disengage said first component to release said focus column from said stage.

12. A subassembly according to claim 11, wherein said second component is configured to engage said first component to pull said focus column toward said stage.

13. A subassembly according to claim 9, wherein the stage has a pocket formed therein for facilitating the receiving of said lower end.

14. A gem microscope comprising the subassembly recited in claim 9.

15. A subassembly for a gem microscope, said subassembly comprising:
    a focus column having a lower end;
    a stage for receiving said lower end;
    a quick disconnect mechanism for removably coupling of said focus column to said stage, said quick disconnect mechanism being externally accessible to a user;
    an alignment pin coupled to said lower end; and means, located on said stage, for receiving said alignment pin to establish lateral alignment of said focus column relative to said stage.

16. A subassembly for a gem microscope, said subassembly comprising:
a focus column having a lower end;
a stage for receiving said lower end; and
a quick disconnect mechanism for removably coupling of said focus column to said stage, said quick disconnect mechanism being externally accessible to a user, wherein said quick disconnect mechanism comprises:
a first component coupled to said lower end of said focus column; and
a second component configured to engage said first component to secure said focus column to said stage and to disengage said first component to release said focus column from said stage, and wherein:
said first component comprises a threaded element that protrudes from said lower end;
said stage includes a hole formed therein, said hole being sized to receive said threaded element; and
said second component comprises a thumbwheel having a threaded insert compatible with said threaded element, said thumbwheel being configured for removably coupling to said threaded element.

17. A subassembly for a gem microscope, said subassembly comprising:
a focus column having a lower end;
a stage;
a threaded element coupled to said lower end, said threaded element protruding from said lower end;
a hole formed within said stage, said hole being sized to receive said threaded element; and
a thumbwheel having a threaded insert compatible with said threaded element, said thumbwheel being configured for removably coupling to said threaded element to connect/disconnect said focus column to/from said stage.

18. A subassembly according to claim 17, further comprising a cavity formed within said stage, said cavity being configured to accommodate said thumbwheel, and said hole providing access to said cavity for said threaded element.

19. A subassembly according to claim 17, wherein said stage comprises a pocket formed therein for receiving said lower end.

20. A subassembly according to claim 17, wherein:
said focus column comprises a mounting surface located at said lower end, and an alignment pin coupled to said lower end;
said stage comprises a number of mounting elements, said mounting elements being configured to establish a mounting plane for said focus column when in contact with said mounting surface; and
said stage comprises means for receiving said alignment pin to establish lateral alignment of said focus column relative to said stage.

21. A gem microscope comprising the subassembly recited in claim 17.

22. A gem microscope comprising:
a focus column;
a gem microscope stage;
and one or more mounting elements on the stage,
wherein the focus column comprises:
a lower end;
a mounting surface located at said lower end, said mounting surface corresponding to a mounting plane for said focus column;
a spaced-apart alignment pin and coupling element pair coupled to, and protruding from, said lower end, said alignment pin being configured to establish lateral alignment of said focus column; and
said coupling element being configured to secure said focus column to the a gem microscope stage.

23. A gem microscope comprising:
a focus column;
a stage;
one or more mounting elements on the stage,
wherein the stage comprises:
a number of mounting elements corresponding to a focus column mounting plane;
a spaced apart alignment pin and threaded coupling element pair for establishing lateral alignment of a gem microscope focus column relative to said stage; and
a cavity formed within said stage, said cavity being configured to accommodate a focus column securing component.

* * * * *